US008940920B2

(12) United States Patent
Lopp et al.

(10) Patent No.: US 8,940,920 B2
(45) Date of Patent: Jan. 27, 2015

(54) METHOD FOR PREPARATION OF (2-HYDROXY-3-OXO-CYCLOPENT-1-ENYL)-ACETIC ACID ESTERS

(71) Applicant: Tallinn University of Technology, Tallinn (EE)

(72) Inventors: Margus Lopp, Tallinn (EE); Anne Paju, Tallinn (EE); Katharina Matkevitš, Tallinn (EE)

(73) Assignee: Tallinn University of Technology, Tallinn (EE)

( * ) Notice: Subject to any disclaimer, the term of this patent is extended or adjusted under 35 U.S.C. 154(b) by 0 days.

(21) Appl. No.: 13/923,495

(22) Filed: Jun. 21, 2013

(65) Prior Publication Data
US 2014/0378698 A1  Dec. 25, 2014

(51) Int. Cl.
C07C 67/313 (2006.01)
C07C 67/333 (2006.01)
C07C 67/343 (2006.01)

(52) U.S. Cl.
CPC .................................. *C07C 67/343* (2013.01)
USPC ........................................................ 560/122

(58) Field of Classification Search
CPC .... C07C 69/738; C07C 67/333; C07C 67/313
USPC ........................................................ 560/122
See application file for complete search history.

(56) References Cited

U.S. PATENT DOCUMENTS 8,148,568 B2   4/2012   Lopp et al.

FOREIGN PATENT DOCUMENTS

| CN | 1927853 | 3/2007 |
| CN | 1948299 | 4/2007 |
| EE | 04848 | 6/2007 |
| EE | 5449 | 8/2011 |
| EP | 0278914 A3 | 8/1990 |
| JP | 2005075734 | 3/2005 |

OTHER PUBLICATIONS

Strassman, M.; Ceci, L.N. Enzymatic formation of homocitric acid, an intermediate in lysine biosynthesis. Biochem. Biophys. Res. Commun., 1964, 14, 262-267.
Strassman, M.; Ceci, L.N. Enzymatic formation of alpha-ketoadipic acid from homoisocitric acid. J. Biol. Chem, 1965, 240, 4357-61.
Hogg, R.W.; Broquist, H.P. Homocitrate formation in *Neurospora crassa*. Relation to lysine biosynthesis. J. Biol. Chem, 1968, 243, 1839-45.
Georgiadis, M.M.; Komiya, H.; Chakrabarti, P.; Woo, D.; Kornuc, J.J.; Rees,D. Crystallographic Structure of the Nitrogenase Iron Protein From Azotobacter-Vinelandii, Science 1992, 257, 1653-59.
Kim, J.; Rees, D.C. Structural Models for the Metal Centers in the Nitrogenase Molybdenum-Iron Protein Science 1992, 257, 1677-82.
Einsle, O.; Tezcan, F.A.; Andrade, S.L.A.; Schmid, B.; Yoshida, M.; Howard, J.B; Rees, D.C. Nitrogenase MoFe-protein at 1.16 angstrom resolution: A central ligand in the FeMo-cofactor Science 2002, 297, 1696-1700.
Maragoudakis, M., Strassman, M. Homocitric acid accumulation by a lysine-requiring yeast mutant J. Biol. Chem., 1966, 241, 695-9.
Li, Z.-C.; Xu, J.-Q. An improved synthesis of homocitrate Molecules, 1998, 3, 31-34.
Ancliff, R.A., Rusell, T.A., J.Sanderson, A.J. Resolution of a citric acid derivative: synthesis of (R)-(−)-homocitric acid-gamma-lactone Tetrahedron: Asymmetry, 1997, 8, 3379-82.
Thomas, U., Kalaynpur, M.G., Stevens, C.M. The absolute configuration of homocitric acid (2-hydroxy-1,2,4-butanetricarboxylic acid), an intermediate in lysine biosynthesis Biochemistry, 1966, 5, 2513-6.
Rodriguez, G.H., Bielmann J.-F. J. Enantioselective syntheses of (−)- and (+)-homocitric acid lactones Org. Chem. 1996, 61, 1822-24.
Ma, G.; Palmer, D.R.J. Improved asymmetric syntheses of (R)-(−)-homocitrate and (2R,3S)-(−)-homoisocitrate, intermediates in the alpha-aminoadipate pathway of fungi Tetrahedron Lett. 2000, 41, 9209-12.
Xu, P.-F.; Matsumoto, Y.; Ohki, Y.; Tatsumi, K. A facile method for synthesis of (R)-(−)- and (S)-(+)-homocitric acid lactones and related alpha-hydroxy dicarboxylic acids from D- or L-malic acid Tetrahedron Letters, 2005, 46, 3815-18.
Paju, A.; Kanger, T.; Pehk, T.; Eek, M.; Lopp, M. A short enantioselective synthesis of homocitric acid-gamma-lactone and 4-hydroxy-homocitric acid-gamma-lactones Tetrahedron, 2004, 60, 9081-84.
Reile I., Paju, A.; Eek, M.; Pehk, T.; Lopp, M. Aerobic Oxidation of Cyclopentane-1,2-diols to Cyclopentane-1,2-diones on Pt/C Catalyst. Synlett, 2008 (3), 347-350.
Prokop, M., Milewska, M.J. An Improved Synthesis of Trisodium (R)-Homocitrate from Citric Acid Polish Journal of Chemistry, 2009, 83, 1317-1322.

Primary Examiner — Yevegeny Valenrod
(74) Attorney, Agent, or Firm — Gearhart Law, LLC

(57) ABSTRACT

The invention relates to the method of preparation of compounds of formula I, the precursors of homocitric acid lactone and its salts, by coupling of the compounds of formula II with bromoacetic acid esters of formula III.

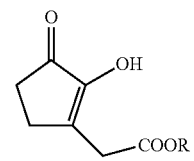

I

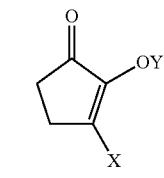

II

BrCH$_2$COOR

III

19 Claims, No Drawings

METHOD FOR PREPARATION OF (2-HYDROXY-3-OXO-CYCLOPENT-1-ENYL)-ACETIC ACID ESTERS

PRIORITY

This application does not claim priority of any previous applications.

FIELD OF THE INVENTION

The present invention relates to preparation of (2-hydroxy-3-oxo-cyclopent-1-enyl)-acetic acid esters: more exactly the present invention relates to a method of the chemical synthesis of (2-hydroxy-3-oxo-cyclopent-1-enyl)-acetic acid esters from 3-halogeno-2-hydroxy-cyclopent-2-en-1-ones or 3-halogeno-2-hydroxy-cyclopent-2-en-1-ones as the starting compounds, by means of a coupling reaction of the starting compounds with Zn derivatives of bromoacetic acid esters. The target compounds, (2-hydroxy-3-oxo-cyclopent-1-enyl)-acetic acid esters, are precursors of (−)-homocitric acid γ-lactone and the corresponding homocitric acid salts.

BACKGROUND OF THE INVENTION (−)-R-Homocitric acid lactone is an intermediate of biosynthesis of lysine in yeast and some fungi (Strassman, M.; Ceci, L. N. *Biochem. Biophys. Res. Commun.*, 1964, 14, 262. Strassman, M.; Ceci, L. N. *J. Biol. Chem*, 1965, 240, 4357. Hogg, R. W.; Broquist, H. P. *J. Biol. Chem*, 1968, 243, 1839). That pathway is absent in plants and mammalians. Homocitric acid is also an important component of the FeMo-cofactor in nitrogenase, which is fixing air nitrogen (Georgiadis, M. M.; Komiya, H.; Chakrabarti, P.; Woo, D.; Kornuc, J. J.; Rees, D. *Science* 1992, 257, 1653. Kim, J.; Rees, D. C. *Science* 1992, 257, 1677. Einsle, O.; Tezcan, F. A.; Andrade, S. L. A.; Schmid, B.; Yoshida, M.; Howard, J. B; Rees, D. C. *Science* 2002, 297, 1696.).

Racemic homocitric acid has been synthesized starting from diethyl-α-ketoadipate cyanohydrin (Maragoudakis, M., Strassman, M. *J. Biol. Chem.*, 1966, 241, 695) and also from ethyl tert-butyl malonate in a three step procedure in 54% yield (Li, Z.-C.; Xu, J.-Q. *Molecules*, 1998, 3, 31).

The enantiomers of homocitric acid have obtained by resolution of racemates that were obtained from the chemical synthesis in 10% overall yield (Ancliff, R. A., Rusell, T. A., J. Sanderson, A. J. *Tetrahedron: Asymmetry*, 1997, 8, 3379).

S-homocitric acid have been obtained as an analytical sample by chemical synthesis starting from optically active (−)-quinic acid (Thomas, U., Kalaynpur, M. G., Stevens, C. M. *Biochemistry*, 1966, 5, 2513). Also, S- and R-enantiomers of homocitric acid γ-lactones have been chemically synthesized starting from natural enantiomeric L-lactic acid and L-serine in a multistep procedure in low overall yield (Rodriguez, G. H., Bielmann J.-F. *J. Org. Chem.* 1996, 61, 1822).

The R-enantiomer of homocitric acid sodium salt was preparatively synthesized from D-malic acid Na-salt in 12% yield using a multiple step procedure (Ma, G.; Palmer, D. R. J. *Tetrahedron Lett.* 2000, 41, 9209). An improved synthesis of R-homocitric acid and 5-homocitric acid from natural D- and L-malic acid correspondingly in a three step procedure in 32-33% overall yield was accomplished (Xu, P.-F.; Matsumoto, Y.; Ohki, Y.; Tatsumi, K. *Tetrahedron Letters*, 2005, 46, 3815 Xu, P.-F.; Tatsumi, K. *Japan Patent Application*, 2005, JP2005-075734). Also, a method for preparation of R-homocitric acid trisodium salt from citric acid has been reported (Prokop, M., Milewska, M. J. *Polish Journal of Chemistry*, 2009, 83, 1317-1322).

A process for preparation of racemic homocitic acid lactone is known (Cai, Qirui Chen, Cai Qirui, Chen Hongbin, Huang Peiqiang, Zhou Zhaohui. Preparation of racemic homocitric acid lactone CN 1948299 (A) 2007-04-18). According to this method (±)-homocitric acid lactone is prepared starting from 2-oxoglutaric acid. Also, a similar patent for the synthesis of racemic homocitic acid lactone starting similarly from 2-ketoglutaric acid is known (Peiquiang, Chen Huang, Huang Peiqiang, Chen Lingyan, Zhang Honkui, CN1927853 (A) 2007-03-14). A method for synthesis of optically active homocitric acid starting from malic acid is known (Tatsumi Kazuyuki, Suu Penfei, Method for producing optically active homocitric acid. JP 2005075734 (A)).

An asymmetric synthesis procedure for optically active R- and S-homocitric acid starting from an achiral 3-hydroxyethyl cyclopentane-1,2-dione is described in Paju, A.; Kanger, T.; Pehk, T.; Eek, M.; Lopp, M. *Tetrahedron*, 2004, 60, 9081. Lopp, M.; Paju, A.; Pehk, T.; Eek, M.; Kanger, T. Estonian Patent EE 04848 B1. Another asymmetric synthesis procedure for R-homocitric acid and S-homocitric acid lactones and salts, starting from achiral (2-hydroxy-3-oxo-cyclopent-1-enyl)-acetic acid esters is also known (Lopp, M.; Paju, A.; Eek, M.; Laos, M; Pehk, T. Estonian Patent EE05449B1; U.S. Pat. No. 8,148,568 B2). According to this procedure the starting compounds are (2-hydroxy-3-oxo-cyclopent-1-enyl)-acetic acid esters, which are transformed to the target compounds homocitric acid lactone and homocitric acid salts by using asymmetric oxidation procedure. The preparation of the starting compounds (2-hydroxy-3-oxo-cyclopent-1-enyl)-acetic acid esters is not described.

The only publication describing the preparation procedure of (2-hydroxy-3-oxo-cyclopent-1-enyl)-acetic acid esters, particularly the corresponding tAm ester is described by Reile et al. (Reile I., Paju, A.; Eek, M.; Pehk, T.; Lopp, M. Aerobic Oxidation of Cyclopentane-1,2-diols to Cyclopentane-1,2-diones on Pt/C Catalyst. *Synlett*, 2008 (3), 347-350). According to that procedure 2-cyclopentene-1-acetic acid is transformed to 2-cyclopentene-1-acetic acid tAm ester by transesterification according to a known procedure (Frei, U., Kirchmayr, R. EP 0278914). The resulted 2-cyclopentene-1-acetic acid tAm ester is dihydroxylated by using fiber bound $OsO_4$ (0.1 mol %) and NMO (1.3 equiv) in $H_2O$-tBuOH 1:3 mixture at 60° C., resulting in (2,3-dihydroxycyclopentenyl)-acetic acid tAm ester. This compound is oxidized with air oxygen in the presence of 5 mol % Pt/C catalyst in MeCN—$H_2O$ 1:1 mixture, in the presence of 1 equivalent of LiOH. The target compound (2-hydroxy-3-oxo-cyclopent-1-enyl)-acetic acid tAm ester was obtained in 28% yield after separation and purification.

There is a need to novel and economic methods to produce 2-hydroxy-3-oxo-cyclopent-1-enyl)-acetic acid esters, which are the starting compounds in the industrial production of homocitric acid. Homocitric acid is a nitrogenase co-factor, which is used in production of nitrogen fertilizers from air nitrogen.

SUMMARY OF THE INVENTION

The aim of the present invention is to develop a simple and efficient method for the synthesis of (2-hydroxy-3-oxo-cyclopent-1-enyl)-acetic acid esters of formula I, which are the starting compounds for the asymmetric synthesis of homocitric acid γ-lactone and the corresponding homocitric acid salts. The aim is reached by using new starting compounds, 3-halogeno-2-hydroxy-cyclopent-2-en-1-ones of formula II. These compounds are transformed into the target compound of formula I by coupling of the starting compounds of formula II with Zn derivatives of halogenoacetic acid esters of formula III, in the presence of Pd catalyst, followed by selective hydrolysis and separation of the product.

It is an object of this invention to A method for preparation of (2-hydroxyl-3-oxo-cyclopent-1-enyl)-acetic acid esters of formula I

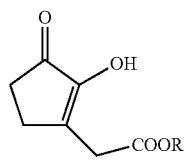

wherein R is an alkyl group, by the use of 3-halogeno-cyclopentane-1,2-diones of formula II as a starting compound

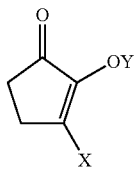

wherein:

X is a halogen atom, and

Y is H, or a substituted Si atom with $R_1$, $R_2$, $R_3$-substitutions, where $R_1$, $R_2$ and $R_3$ are all $CH_3$; or $R_1$ and $R_2$ are both $CH_3$, and $R_3$=tBu, for the synthesis of (2-hydroxyl-3-oxo-cyclopent-1-enyl)-acetic acid esters of formula I.

DETAILED DESCRIPTION OF THE INVENTION

According to the present invention achiral (2-hydroxy-3-oxo-cyclopent-1-enyl)-acetic acid esters formula I

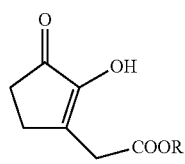

where R is a primary alkyl group, such as $CH_3$, $C_2H_5$, etc, preferably an alkyl group up to 5 carbon atoms; or R is a primary alkylphenyl group such as $CH_2$-Ph; or R is a tertial alkyl group such as —$C(CH_3)_3$, $C(CH_3)_2C_2H_5$, etc. are obtained by using a compound of formula II as a starting compound

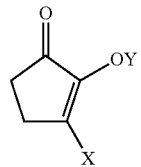

where X is a halogen atom, preferably Cl or Br or I, and Y is H, or a substituted Si atom with substituents $R_1R_2R_3$, where $R_1$, $R_2$ and $R_3$ are all $CH_3$; or $R_1$=$R_2$=$CH_3$ and $R_3$=tBu, for the synthesis of (2-hydroxyl-3-oxo-cyclopent-1-enyl)-acetic acid esters of formula I.

According to the invention compound formula II is coupled with one or more Zn derivatives of the bromoacetic acid esters of formula III, where ester alkyl group R is a primary alkyl group like $CH_3$, $C_2H_5$, etc., preferably an alkyl group up to 5 carbon atoms; or a primary alkylphenyl group like $CH_2$-Ph; or tertial alkyl groups like $C(CH_3)_3$, $C(CH_3)_2C_2H_5$.

$$BrCH_2COOR \qquad III$$

A general scheme of the preparation of the target compound of formula I by using Zn derivatives of bromacetic acid esters of formula III and starting from the compound of formula II is outlined in the Scheme 1.

Scheme 1. A general scheme of preparation of compounds formula I.

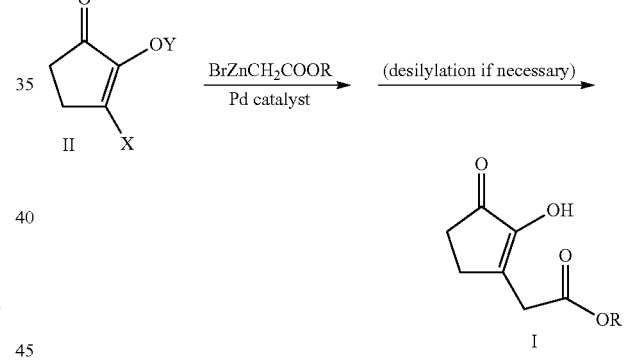

According to the invention the target compound is prepared by a coupling of the starting compound of formula II with one or more Zn derivatives of bromoacetic acid ester of formula III. According to the invention bromoacetic acid ester of formula III is converted to Zn derivative with Zn dust in an organic solvent like terahydrofuran (THF), dioxane or other aprotonic organic solvent. According to the preferred embodiment of present invention the organic solvent is THF.

The coupling reaction of the starting compound of formula II and Zn derivatives of bromoacetic acid ester of formula III is catalyzed by addition of a Pd catalyst. The Pd catalyst is selected from the group of soluble in organic solvent Pd catalysts like $Pd_2dba_3$ (Tris(dibenzylideneacetone)dipalladium(0)), $Pd(OAc)_2$, $P(t-Bu_3)PdBr_2$. According to the preferred embodiment of present invention the Pd catalyst is $Pd_2dba_3$. The ratio of the Pd catalyst to substrate is 1-10 molar %, and most preferably 5 molar %.

The presence of a phosphorus-containing ligand to the Pd catalyst is essential for the present invention. The phosphorous ligand is selected from the following group of compounds: Q-phos (1,2,3,4,5-Pentaphenyl-1'-(di-tert-butylphosphino)ferrocene), X-phos (2-Dicyclohexylphosphino-2',4',6'-triisopropylbiphenyl), bpdbp ((2-biphenyl)di-tert-butylphosphine), Pd(PPh$_3$)$_4$. According to the preferred embodiment of present invention the phosphorous ligand is Q-phos. The amount of the ligand corresponds to the amount of the Pd catalyst and is approximately equimolar to it.

The ratio of Zn derivative and substrate is essential for the present invention. According to the preferred embodiment of present invention the range of Zn derivative to substrate 2:1 to 3:1.

The reaction temperature is not essential for the present invention. According to the preferred embodiment of present invention the reaction temperature is around the ambient temperature. Also, the reaction time is not essential according to this invention: reaction time is selected to achieve conversion of the starting compounds.

The reaction is quenched with NH$_4$Cl solution, extracted with organic solvent and concentrated. These conditions and choice of an extraction solvent are not essential for the present invention. Extract is concentrated and purified, to afford the target compound I.

In the case of compounds II where Y is SiR$_1$R$_2$R$_3$, the concentrated extract is subjected to desilylation in an organic solvent by the use of a fluorine-containing reactant. The choice of the organic solvent and the fluorine-containing reactant are not essential for the present invention. According to the preferred embodiment of present invention the organic solvent is THF and the fluorine containing reagent is tetrabutylammonium fluoride (TBAF). Close to equimolar amount of TBAF is used as a 1 M solution in THF. The reaction is quenched with saturated NH$_4$Cl solution and the aqueous phase is extracted with organic solvent. These conditions are not essential to this invention. According to the preferred embodiment of present invention the solvent is ethyl acetate (EtOAc). The extract is concentrated and purified, to afford the target compound I.

The invention is now described with non limiting examples.

EXAMPLES

Example 1

Synthesis of (2-Hydroxy-3-oxo-cyclopent-1-enyl)-acetic acid tert-butyl ester from 3-bromo-2-cyclopent-2-en-1-one A solution of tert-butyl bromoacetate (1.5 mmol, 221 µL) in 1.8 mL THF was added at rt to an argon purged flask containing a suspension of zinc dust. (3 mmol, 196 mg) in THF (1.2 mL). The suspension was stirred for 1 h, then the zinc was allowed to settle and 3 ml of supernatant was transferred through a septum to a mixture of 3-bromo-2-cyclopent-2-en-1-one (88.5 mg, 0.5 mmol), Pd$_2$dba$_3$ (23 mg, 5 mol %), Q-phos (18 mg, 5 mol %) in THF 1 mL under Ar. The mixture was stirred for 12 h and then quenched with 1M NH$_4$Cl (40 mL) and extracted with CH$_2$Cl$_2$. The combined organic layers were dried over MgSO$_4$, filtered and the solvent evaporated. The residue was chromatographed on a silica gel column (EtOAc/Hept). White crystals were obtained. $^1$H TMR (500 MHz, CDCl$_3$): δ 6.78 (s, 1H, OH), 3.36 (s, 2H, CH$_2$CO), 2.53 (m, 2H, H-5), 2.42 (m, 2H, H-4), 1.44 (s, 9H, tert-Bu); $^{13}$C TMR (125 MHz, CDCl$_3$): δ 203.08 (C-3), 168.86 (COO), 150.04 (C-2), 138.50 (C-1), 81.71 (OC (Me)$_3$), 35.48 (CH$_2$CO), 32.01 (C-4), 27.95 (OC(Me)$_3$), 25.30 (C-5). MS (EI): m/z=212 (M$^+$), 156, 139, 111, 82, 57. IP v=3307, 2999, 2973, 1728, 1699, 1665, 1415, 1384, 1366, 1151 cm$^{-1}$. MS (EI): m/z=212 (M$^+$), 156, 139, 111, 82, 57, 41, 29. IR (cm$^{-1}$) 3307, 2999, 2973, 1728, 1699, 1665, 1415, 1384, 1366, 1151, 699 cm$^{-1}$.

Example 2

Synthesis of (2-Hydroxy-3-oxo-cyclopent-1-enyl)-acetic acid tert-butyl ester from 3-bromo-2-(tert-butyl-dimethyl-silanyloxy)-cyclopent-2-en-1-one To a solution of 3-bromocyclopentane-1,2-dione (446 mg, 2.52 mmol) and imidazole (343 mg, 5.04 mmol) in CH$_2$Cl$_2$ (12.5 mL) at 0° C. TBDMSCl (571 mg, 3.78 mmol) was added. After stirring at 0° C. for 30 min, water (25 mL) was added, CH$_2$Cl$_2$-layer was separated and the aqueous was extracted with CH$_2$Cl$_2$ (2×15 mL). The combined extracts were washed with brine (15 mL), dried (Na$_2$SO$_4$) and concentrated. The residue was purified by flash chromatography (silica gel, heptane/EtOAc 60:1 to 50:1) to give a white solid (662 mg, 90%); m.p. 54-55° C.; $^1$H NMR (400 MHz, CDCl$_3$): δ 2.82-2.80 (m, 2H, H-4), 2.51-2.49 (m, 2H, H-5), 0.98 (s, 9H, tert-Bu), 0.22 (s, 6H, Si(Me)$_2$); $^{13}$C NMR (101 MHz, CDCl$_3$) δ 198.6 (C-1), 151.9 (C-2), 136.1 (C-3), 34.1 (C-5), 30.0 (C-4), 25.7 (SiC(Me)$_3$), 18.5 (SiC(Me)$_3$), −3.9 (Si(Me)$_2$); IR (KBr, cm$^{-1}$): 2958, 2929, 2859, 1706, 1632, 1474, 1408, 1332, 1300, 1247, 1158, 1077, 896, 845, 785; MS (m/z, %): 277, 275, 236, 235 (base), 234, 233 (base), 234, 233 (base), 193, 191, 154, 139, 137, 125, 111, 73, 57.

A solution of tert-butyl bromoacetate (1.5 mmol, 221 µL) in 1.8 mL THF was added at room temperature to an argon purged flask containing a suspension of zinc dust. (3 mmol, 196 mg) in THF (1.2 mL). The suspension was stirred for 1 h, then the zinc was allowed to settle and 3 ml of supernatant was transferred through a septum to a mixture of 3-bromo-2-(tert-butyl-dimethyl-silanyloxy)-cyclopent-2-en-1-one (145.5 mg, 0.5 mmol), Pd$_2$dba$_3$ (23 mg, 5 mol %), Q-phos (18 mg, 5 mol %) in THF 1 mL under Ar. The mixture was stirred for 12 h and then quenched with 1M NH$_4$Cl (40 mL) and extracted with CH$_2$Cl$_2$. The combined organic layers were dried over MgSO$_4$, filtered and the solvent evaporated. The residue was chromatographed on a silica gel column (EtOAc/Hept). White crystals were obtained. Yield: 125 mg, 77%. Mp 87-88° C.

(2-(tert-Butyl-dimethyl-silanyloxy)-3-oxo-cyclopent-1-enyl)-acetic acid tert-butyl ester (0.147 mmol, 48 mg) was dissolved in 2 mL of THF under Ar atmosphere and treated with 0.162 mL of 1 M TBAF solution in THF. After 10 min of stirring of the reaction mixture it was quenched with 3 mL of saturated NH$_4$Cl solution, the phases separated and the aqueous phase extracted twice with 2 mL of EtOAc. The organic phases were combined, dried over MgSO$_4$, the solvent was evaporated and the product purified by column chromatography on silica gel (EtOAc/Heptane). White crystals were obtained. $^1$H TMR (500 MHz, CDCl$_3$): δ 6.78 (s, 1H, OH), 3.36 (s, 2H, CH$_2$CO), 2.53 (m, 2H, H-5), 2.42 (m, 2H, H-4), 1.44 (s, 9H, tert-Bu); $^{13}$C TMR (125 MHz, CDCl$_3$): δ 203.08 (C-3), 168.86 (COO), 150.04 (C-2), 138.50 (C-1), 81.71 (OC (Me)$_3$), 35.48 (CH$_2$CO), 32.01 (C-4), 27.95 (OC(Me)$_3$), 25.30 (C-5). MS (EI): m/z=212 (M$^+$), 156, 139, 111, 82, 57. IP v=3307, 2999, 2973, 1728, 1699, 1665, 1415, 1384, 1366, 1151 cm$^{-1}$. MS (EI): m/z=212 (M$^+$), 156, 139, 111, 82, 57, 41, 29. IR (cm$^{-1}$) 3307, 2999, 2973, 1728, 1699, 1665, 1415, 1384, 1366, 1151, 699 cm$^{-1}$.

Example 3

Synthesis of (2-Hydroxy-3-oxo-cyclopent-1-enyl)-acetic acid ethyl ester from 3-bromo-2-(tert-butyl-dimethyl-silanyloxy)-cyclopent-2-en-1-one According to procedure of Example 2, (2-hydroxy-3-oxo-cyclopent-1-enyl)-acetic acid ethyl ester was prepared from 3-bromo-2-(tert-butyl-dimethyl-silanyloxy)-cyclopent-2-en-1-one and bromoacetic acid ethyl ester. The compound has the following physical parameters: $^1$H TMR (500 MHz, CDCl$_3$): δ 6.20 (bs, 1H, OH), 4.17 (q, J=7.3 Hz, 2H, OCH$_2$CH$_3$), 3.45 (s, 2H, CH$_2$CO), 2.55 (m, 2H, H-5), 2.45 (m, 2H, H-4), 1.26 (t, J=7.3 Hz, 3H, OCH$_2$CH$_3$); $^{13}$C TMR (125 MHz, CDCl$_3$): δ 203.25 (C-3), 169.60 (COO), 150.14 (C-2), 138.10 (C-1), 61.24 (OCH$_2$CH$_3$), 34.12 (CH$_2$CO), 32.00 (C-4), 25.28 (C-5), 14.04 (CH$_2$CH$_3$).

Example 4

Synthesis of (2-hydroxy-3-oxo-cyclopent-1-enyl)-acetic acid methyl ester from 3-bromo-2-(tert-butyl-dimethyl-silanyloxy)-cyclopent-2-en-1-one According to procedure of Example 2, (2-hydroxy-3-oxo-cyclopent-1-enyl)-acetic acid methyl ester was prepared 3-bromo-2-(tert-butyl-dimethyl-silanyloxy)-cyclopent-2-en-1-one and bromoacetic acid methyl ester. (2-hydroxy-3-oxo-cyclopent-1-enyl)-acetic acid methyl ester has the following physical parameters: $^1$H TMR (500 MHz, CDCl$_3$): δ 6.45 (bs, 1H, OH), 3.73 (s, 3H, OMe), 3.47 (s, 2H, CH$_2$CO), 2.56 (m, 2H, H-5), 2.46 (m, 2H, H-4); $^{13}$C TMR (125 MHz, CDCl$_3$): δ 202.83 (C-3), 169.96 (COO), 150.09 (C-2), 137.20 (C-1), 52.20 (OMe), 33.86 (CH$_2$CO), 31.97 (C-4), 25.29 (C-5). MS (EI): m/z (%)=170 (M$^+$, 47), 138 (100), 111 (59), 110 (52), 82 (57), 59 (25), 55 (72). IR (cm$^{-1}$): 3314, 2961, 1730, 1700, 1656, 1438, 1391, 1270, 1224, 1114 cm$^{-1}$.

Example 5

Synthesis of (2-Hydroxy-3-oxo-cyclopent-1-enyl)-acetic acid benzyl ester from 3-bromo-2-(tert-butyl-dimethyl-silanyloxy)-cyclopent-2-en-1-one According to procedure of Example 2, (2-hydroxy-3-oxo-cyclopent-1-enyl)-acetic acid benzyl ester was prepared from 3-bromo-2-(tert-butyl-dimethyl-silanyloxy)-cyclopent-2-en-1-one and bromoacetic acid benzyl ester. (2-Hydroxy-3-oxo-cyclopent-1-enyl)-acetic acid benzyl ester has the following physical parameters: $^1$H NMR (400 MHz, CDCl$_3$) δ 7.41-7.30 (m, 5H, Ph), 6.24 (s, 1H, OH), 5.17 (s, 2H, CH$_2$Ph), 3.51 (s, 2H, CH$_2$COO), 2.56-2.50 (m, 2H, H-5), 2.46-2.41 (m, 2H, H-4). $^{13}$C NMR (101 MHz, CDCl$_3$) δ 203.00 (C-3), 169.54 (CH$_2$COO), 150.24 (C-2), 137.26 (C-1), 135.53 (Ph), 128.76 (Ph), 128.59 (Ph), 128.47 (Ph), 67.20 (CH$_2$Ph), 34.27 (CH$_2$COO), 32.13 (C-4), 25.45 (C-5).

Example 6

Synthesis of (2-hydroxy-3-oxo-cyclopent-1-enyl) acetic acid tert-amyl ester from 3-bromo-2-(tert-butyl-dimethyl-silanyloxy)-cyclopent-2-en-1-one According to procedure of Example 2, (2-hydroxy-3-oxo-cyclopent-1-enyl)-acetic acid tert-amyl ester was prepared from 3-bromo-2-(tert-butyl-dimethyl-silanyloxy)-cyclopent-2-en-1-one and bromoacetic acid tert-amyl ester. (2-Hydroxy-3-oxo-cyclopent-1-enyl)-acetic acid tert-amyl ester has the following physical parameters: $^1$H TMR (500 MHz, CDCl$_3$): δ 6.85 (s, 1H, OH), 3.38 (s, 2H, CH$_2$CO), 2.53 (m, 2H, H-5), 2.43 (m, 2H, H-4), 1.75 (q, J=7.3 Hz, 2H, CH$_2$CH$_3$), 1.42 (s, 6H, (CH$_3$)$_2$), 0.86 (t, J=7.3 Hz, 3H, CH$_2$CH$_3$). $^{13}$C TMR (125 MHz, CDCl$_3$): δ 203.16 (C-3), 168.80 (COO), 150.04 (C-2), 138.61 (C-1), 84.24 (OC(Me)$_2$), 35.42 (CH$_2$CO), 33.36 (CH$_2$CH$_3$), 32.01 (C-4), 25.36 (OC(Me)$_2$ ja C-5), 8.09 (CH$_3$CH$_2$). MS (EI): m/z (%)=226 (M$^+$), 156 (24), 139 (23), 111 (20), 71 (66), 55 (19), 43 (100). IP v=3315, 2979, 2937, 2885, 1727, 1699, 1665, 1465, 1386, 1193, 1149 cm$^{-1}$.

What is claimed is:

1. A method for preparation of (2-hydroxyl-3-oxo-cyclopent-1-enyl)-acetic acid esters of formula I

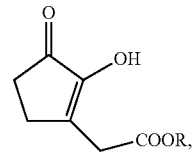

wherein R is an alkyl group, or an alkyl phenyl group,
said method comprising the steps of:
a) selecting 3 halogeno-cyclopentane-1,2-diones of formula II as a starting compound

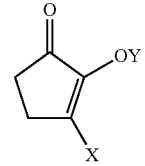

wherein:
X is a halogen atom, and
Y is H, or a substituted Si atom with $R_1$, $R_2$, $R_3$-substitutions, where $R_1$, $R_2$ and $R_3$ are all CH$_3$; or $R_1$ and $R_2$ are both CH$_3$, and $R_3$=tBu;
b) in presence of a catalyst, coupling the starting compounds of formula II with Zn-derivatives of bromoacetic acid esters of formula III

BrCH$_2$COOR,    III wherein R is alkyl or an alkyl phenyl group; and
c) Obtaining (2-hydroxyl-3-oxo-cyclopent-1-enyl)-acetic acid esters of formula I.

2. The method of claim 1, wherein in formula I R is an alkyl group with 1-5 carbon atoms, a tertial alkyl group —C(CH$_3$)$_3$, or C(CH$_3$)$_2$C$_2$H$_5$, or a primary alkylphenyl group CH$_2$-Ph.

3. The method of claim 1, wherein X is Cl, Br, or I.

4. The method according to claim 1, where substituent R in bromoacetic acid esters formula III is selected from the group consisting of primary alkyls with 1-5 carbon atoms, primary alkylphenyl group —CH$_2$-Ph, and tertial alkyl groups —C(CH$_3$)$_3$, and —C(CH$_3$)$_2$C$_2$H$_5$.

5. The method according to claim 1, where the bromoacetic acid esters formula III are transformed to Zn derivative.

6. The method of claim 5, wherein ratio of the Zn-derivative to starting compound of formula II is between 1:2 and 1:3.

7. The method according to claim 1, where the catalyst is a Pd-containing catalyst.

8. The method of claim 7, wherein the Pd-containing catalyst is selected from the group consisting of $Pd_2dba_3$ (Tris(dibenzylideneacetone)dipalladium(0)), $Pd(OAc)_2$, and $P(t-Bu_3)PdBr_2$.

9. The method according to claim 8, where the Pd catalyst is $Pd_2dba_3$.

10. The method according to claim 7, wherein the ratio of Pd-containing catalyst to substrate is 1-10 molar %.

11. The method according to claim 10, wherein the ratio is 5 molar %.

12. The method of claim 7, wherein the Pd-containing catalyst has a phosphorus-containing ligand.

13. The method of claim 12, wherein the phosphorus-containing ligand is selected from the group consisting of: Q-phos (1,2,3,4,5-Pentaphenyl-1'-(di-tert-butylphosphino)ferrocene), X-phos (2-Dicyclohexylphosphino-2',4',6'-triisopropylbiphenyl), bpdbp ((2-biphenyl)di-tert-butylphosphine), and $Pd(PPh_3)_4$.

14. The method according to claim 13, wherein the phosphorus containing ligand to Pd catalyst is Q-phos.

15. The method of claim 1, wherein reaction temperature is room temperature.

16. The method of claim 2, wherein Y is $SiR_1R_2R_3$ and reaction mixture is subjected to desilylation in an organic solution by use of a fluorine-containing reactant.

17. The method of claim 16, wherein the fluorine containing reactant is tetrabutylammonium fluoride (TBAF) and the organic solvent is THF.

18. The method of claim 17, wherein the reaction is quenched with $NH_4Cl$ and an aqueous phase is extracted with an organic solvent.

19. The method of claim 18, wherein the organic solvent is ethyl acetate.

* * * * *